(12) United States Patent
Lampropoulos et al.

(10) Patent No.: US 7,182,750 B2
(45) Date of Patent: *Feb. 27, 2007

(54) MODULARIZED INFUSION PUMP APPARATUS

(75) Inventors: Fred P. Lampropoulos, Sandy, UT (US); Thomas D. Stout, Salt Lake City, UT (US)

(73) Assignee: Merit Medical Systems, Inc, South Jordan, UT (US)

( * ) Notice: Subject to any disclaimer, the term of this patent is extended or adjusted under 35 U.S.C. 154(b) by 329 days.

This patent is subject to a terminal disclaimer.

(21) Appl. No.: 10/788,945

(22) Filed: Feb. 25, 2004

(65) Prior Publication Data

US 2004/0167471 A1 Aug. 26, 2004

Related U.S. Application Data

(63) Continuation of application No. 10/141,550, filed on May 6, 2002, now Pat. No. 6,800,069.

(51) Int. Cl.
*A61M 37/00* (2006.01)
*A61M 1/00* (2006.01)

(52) U.S. Cl. .................... 604/140; 604/142; 604/151

(58) Field of Classification Search ........ 604/140–141, 604/142, 151
See application file for complete search history.

(56) References Cited

U.S. PATENT DOCUMENTS 4,684,367 A * 8/1987 Schaffer et al. ............. 604/140
5,059,182 A * 10/1991 Laing ......................... 604/142

\* cited by examiner

*Primary Examiner*—Catherine S. Williams
(74) *Attorney, Agent, or Firm*—Workman Nydegger

(57) ABSTRACT

The present invention is directed to a modular pressure infuser apparatus adapted to allow a user to modify the configuration of the pressure infuser apparatus by utilizing one or more interchangeable manual and/or automatic pumps to inflate a pressure infuser bag of the pressure infuser apparatus. The modular configuration of the pressure infuser apparatus permits the user to detach and reattach a motorized pump and/or a manual pump to the pressure infuser bag quickly, easily, and efficiently without decreasing the air pressure of the pressure infuser bag. By providing selectively removable pump modules, the user can select the configuration of the pressure infuser apparatus that is best adapted to the needs of the patient. A pressure release valve is configured to regulate the pressure of the pressure infuser bag.

2 Claims, 7 Drawing Sheets

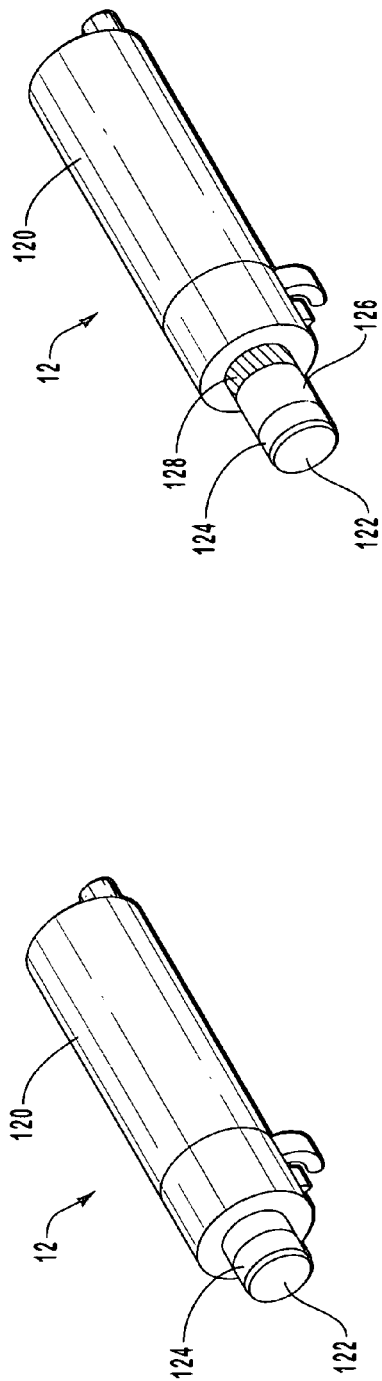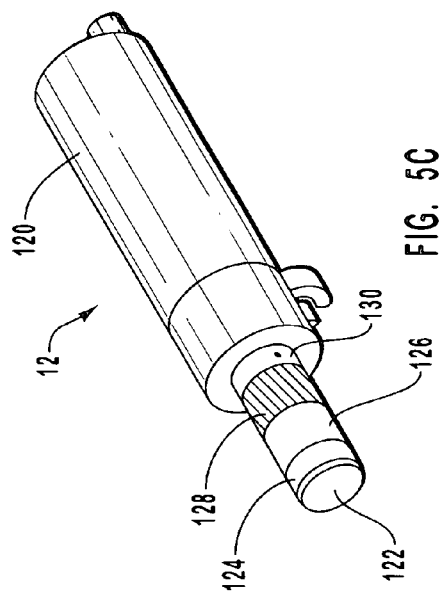

MODULARIZED INFUSION PUMP APPARATUS

CROSS-REFERENCE TO RELATED APPLICATIONS

This application is a continuation of U.S. patent application Ser. No. 10/141,550 entitled, "Modularized Infusion Pump Apparatus" filed May 6, 2002 now U.S. Pat. No. 6,800,069.

BACKGROUND OF THE INVENTION

1. The Field of the Invention

The present invention relates to infusion devices. More particularly the present invention relates to a pressure infuser apparatus for use with an infusion device, the pressure infuser apparatus having a modular configuration allowing a user to interchangeably utilize one or more manual and/or motorized pump modules to modify the configuration of the pressure infuser apparatus to suit the changing infusion needs of a patient.

2. The Relevant Technology

Infusion devices are used for the subcutaneous administration, to humans or animals, of intravenous fluids such as blood, nutrients, medicine, and saline. The fluids are stored and administered from pliant infusate bags typically made from plastic film materials. The infusate bags facilitate the administration of infusate fluids, while limiting the amount of air that is transferred to the patient with the fluid.

Infusion devices allow fluids to be administered to patients in a variety of manners. A common administration technique involves suspending an infusate bag from a hook or peg and allowing gravity to provide the force needed to deliver the fluid to the patient by means of a delivery line. Where suspension administration is utilized, the infusate bag includes an outlet tube at the lower end of the bag. A delivery tube is attached to the outlet tube for delivering the fluid from the bag to the patient. The delivery tube usually includes an observable drop-feed device and an adjustable flow delivery valve for allowing medical staff to regulate the fluid flow rate.

There are limitations to using suspension to administer IV fluids. Where gravitational forces are the sole means of administering fluid, the viscosity of some fluids, such as blood and plasma, makes delivery of the fluid problematic. The problem is exacerbated where the fluid must be delivered quickly and efficiently, as with major traumas where large amounts of blood are required in a short amount of time. To facilitate a higher rate of infusate delivery, such as is required with highly viscous fluids, medical staff utilizes various methods to increase the pressure on the infusate fluid. Examples of such methods include, pressure pumps, inflation cuffs, inflation bladders, or even manual compression of the infusate bag.

Another limitation of suspension administration relates to ambulation of patients. Ambulation can be difficult where an IV pole must be wheeled by the patient or medical staff. The configuration of many IV poles renders them unstable leading to accidents which can cause injury to patients, staff, or bystanders and/or rupture the infusate bag. Not only are the IV poles unstable, they are also inconvenient. It is difficult to maneuver the poles while pushing a wheel chair or hospital bed, particularly where additional medical devices must be transported with the patient. As with the delivery of highly viscous fluids, pressure pumps, inflation cuffs, inflation bladders, and manual compression of the infusate bag allow fluids to be delivered to the patient as needed during ambulation.

Among the methods of providing compression of the infusate bag, pressure infuser bags have been accepted in the medical products industry as an efficient and inexpensive method for providing the pressure required by highly viscous fluids, ambulation, and many other circumstances. Pressure infuser bags comprise an inflatable air bladder with a sleeve or pouch for holding the infusate bag. When the user inflates the air bladder, pressure is exerted on the infusate bag contained in the sleeve, thus providing the pressure needed to deliver the fluid.

A variety of mechanisms have been developed to inflate the pressure infuser bag. The mechanisms have been adapted to meet the requirements of medical staff in a variety of circumstances. For example, one traditional inflation mechanism is the compressible hand bulb. The bulb is comprised of rubber or flexible plastic material with the ends of the bulb having air valves. The bulb is attached to the pressure infuser bag by tubing. A user inflates the pressure infuser bag by compressing and releasing the bulb. The simple construction of many hand bulb mechanisms permits the bulbs to be manufactured quickly and inexpensively. A limitation of such hand pumps is that a user must compress and release the bulb many times to inflate the pressure infuser bag. This is particularly true for larger pressure infuser bags that can have up to a three-liter capacity. The repetitive compression can be both time consuming and fatiguing for users of hand held pumps.

Motorized pneumatic pump mechanisms are configured to quickly inflate the pressure infuser bag with little effort from the user. Some motorized pumps include a one-touch button for inflating the bag to a given pressure. By providing a mechanism to quickly inflate the pressure infuser bag, the medical staff can begin delivery of high amounts of fluids in a very short amount of time. The ability to quickly and efficiently deliver high amounts of fluid is critical in trauma and critical care situations often encountered in critical care units, emergency rooms, and operating rooms. A drawback of motorized pumps is that their configuration makes pressure infuser bags having motorized pumps costly for hospitals to obtain in large quantities.

Hospitals need not provide motorized pumps for every patient in every situation. Many patients require the delivery of high amounts of fluid for a limited and determinable amount of time. For example, a patient requiring the benefits of an pressure infuser bag having a motorized pump while in critical care might need nothing more than a pressure infuser bag having a compressible bulb when the patient is stabilized and being transferred to a step down unit. Problems can be encountered in switching between pressure infuser bags having a motorized pump and pressure infuser bags having a compressible bulb. The time, effort, and complication associated with switching the infuser pumps can make such switching difficult and impractical.

BRIEF SUMMARY OF THE INVENTION

The present invention is directed to a modular pressure infuser apparatus allowing a user to interchangeably utilize one or more manual and/or motorized pump modules to modify the configuration of the pressure infuser apparatus to suit the changing infusion needs of a patient. The modules of the pressure infuser apparatus can include a pressure infuser bag module, a motorized pump module, and a manual pump module. The modular configuration of the pressure infuser apparatus permits the user to detach and reattach the motorized pump and/or the manual pump to the pressure infuser bag quickly, easily, and efficiently without decreasing the air pressure in the pressure infuser bag.

By providing selectively removable pump modules, the user can select the configuration of the pressure infuser apparatus that is best adapted to the needs of the patient. For example, while a patient is in an unstable condition, such as is often encountered in an emergency room, operating room, or critical care unit, medical staff can utilize a motorized pump in conjunction with the pressure infuser bag. The medical staff can also couple the manual pump with the motorized pump and the pressure infuser bag. By having a manual pump and a motorized pump a user can inflate the pressure infuser bag in the event of motorized pump failure.

Once the patient is stabilized and the need for rapid inflation of the pressure inflation bag has passed, the medical staff can simply remove the motorized pump module. This allows the motorized pump module to be utilized for other patients. The ability to remove the motorized pump can be helpful where a stabilized patient is being transferred to a step down or recovery unit where motorized pumps are not typically used. The motorized pump module can remain in the critical care unit, operating room, or emergency room where it will be better utilized.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 5A–C provide a perspective view of pressure release valve illustrating indicia representing the air pressure in the pressure infuser bag.

DETAILED DESCRIPTION OF THE PREFERRED EMBODIMENTS

The present invention is directed to a pressure infuser apparatus adapted to allow a user to modify the configuration of the pressure infuser apparatus by utilizing one or more interchangeable manual and/or motorized pumps to inflate a pressure infuser bag of the pressure infuser apparatus. The pressure infuser apparatus comprises separate modules including a pressure infuser bag module and a plurality of pump modules. In the preferred embodiment the pump modules comprise a motorized pump module and a manual pump module. The types of pumps that can be utilized in the context of the present invention are not limited to motorized pumps and manual pumps. For example, pressurized pumps, chemical pumps, etc. can be utilized without departing from the scope and spirit of the present invention. Similarly, the pressure infuser apparatus is not limited to an air inflatable apparatus. A variety of pressure infuser apparatus can be utilized configured to convey pressure by a variety of mechanisms, including but not limited to, apparatuses utilizing fluids, gases, chemicals, or other the like as the pressure driving mediums.

The modular configuration of the pressure infuser apparatus permits the user to detach and reattach the motorized pump and/or the manual pump to the pressure infuser bag quickly, easily, and efficiently without decreasing the air pressure of the pressure infuser bag. By providing selectively removable pump modules, the user can select the configuration of the pressure infuser apparatus that is best adapted to the needs of the patient. For example, while a patient is in an unstable condition such as is often encountered in an emergency room, operating room, or critical care unit, medical staff can utilize the pressure infuser bag in conjunction with both a motorized pump and a manual pump. Once the patient is stabilized and the need for rapid inflation and/or the ability to automatically maintain the pressure of the pressure infuser bag has passed, the medical staff can simply remove the motorized pump module.

Figure 1:
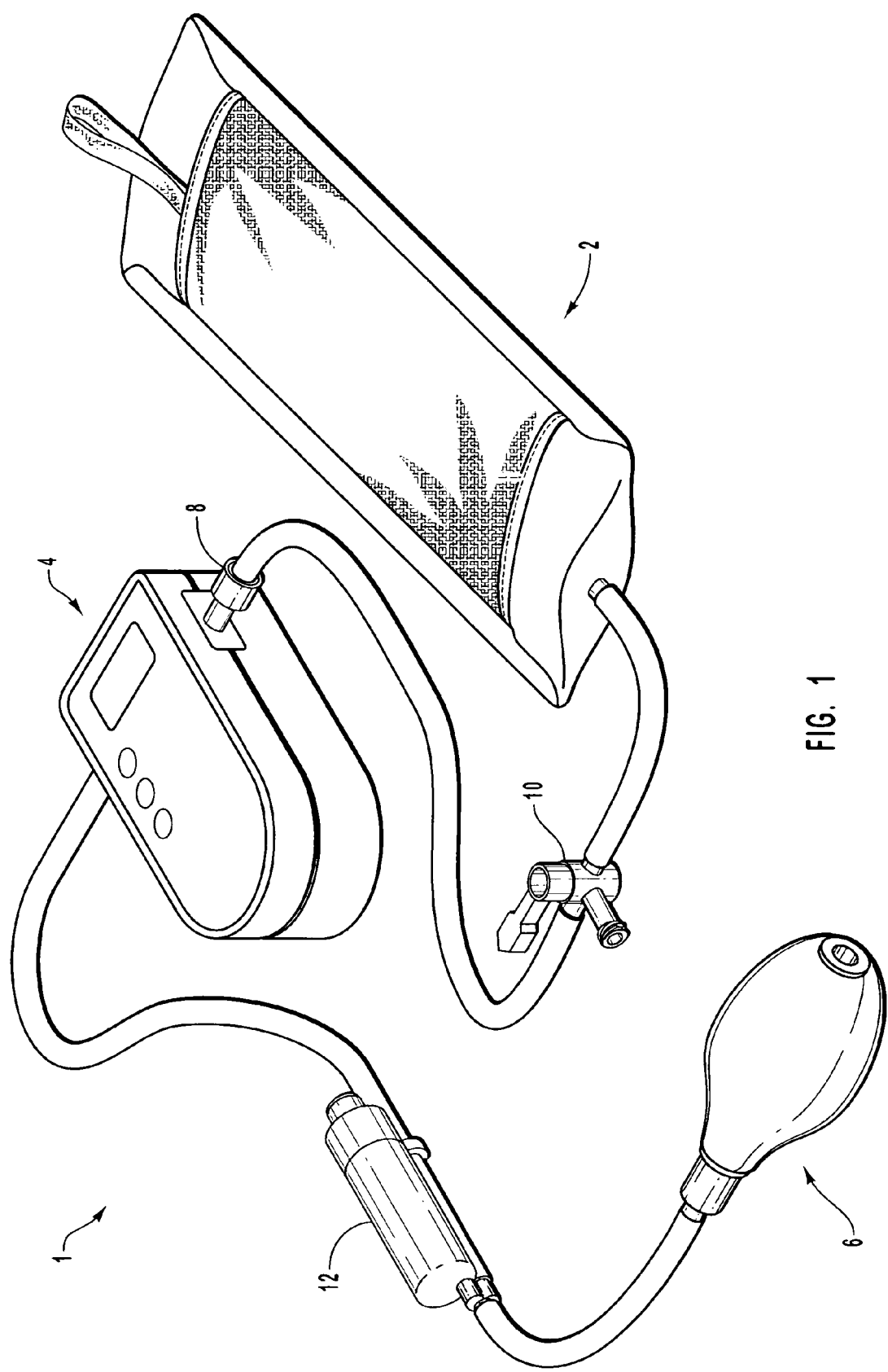
FIG. 1 is a perspective view of the pressure infuser apparatus illustrating a pressure infuser bag module, motorized pump module, and manual pump module in one configuration of the present invention.

FIG. 1 is a perspective view illustrating one configuration of the pressure infuser apparatus 1 of the present invention. Pressure infuser apparatus 1 is adapted to provide pressure to an infusate bag or intravenous bag for facilitating delivery of infusate fluid to a patient. Additional pressure is required on infusate bags or intravenous bags in different situations such as: a) where high amounts of infusate must be delivered in a short amount of time; b) when ambulation of a patient is needed or desired; or c) where the high viscosity of the infusate fluid makes delivery of the infusate slower than is required. Pressure infuser apparatus 1 comprises a pressure infuser bag module 2, a motorized pump module 4, and a manual pump module 6. There is also shown coupler mechanism 8, stop cock 10, and pressure release valve 12.

The modularized configuration of pressure infuser apparatus 1 allows the user to select the configuration of pressure infuser apparatus 1 that is best adapted to the needs of the patient. In the illustrated embodiment, both motorized pump module 4 and manual pump module 6 are coupled to pressure infuser bag module 2. Motorized pump module 4 is directly coupled to pressure infuser bag module 2. Manual pump module 6 is coupled directly to motorized pump module 4 and indirectly to pressure infuser bag module 2.

In the illustrated embodiment two couplers are utilized to connect modules 2, 4, and 6. A first coupler 8 couples motorized pump module 4 to pressure infuser bag module 2. By disconnecting coupler 8, a user is able to remove motorized pump module 4 from pressure infuser bag module 2. A second coupler (not shown) couples manual pump module 6 to motorized pump module 4. The second coupler also allows the user to disconnect manual pump module 6 from motorized pump module 4. Manual pump module 6 can then be connected to pressure infuser bag module 2.

Stop cock 10 is configured to allow a user to maintain the pressure in pressure infuser bag module 2 when manual pump module 6 and/or motorized pump module 4 are disconnected from infuser bag module 2. Stop cock 10 also allows the user to release air pressure in pressure infuser bag module 2 when manual pump module 6 and/or motorized pump module 4 are coupled to pressure infuser bag module 2. In one embodiment stop cock 10 comprises a three-way stop cock configured to be coupled to either motorized pump module 4 or manual pump module 6. Alternative embodiments utilize one or more stop cocks having alternative configurations (See e.g. FIG. 6).

Pressure release valve 12 is configured to prevent the pressure of pressure infuser bag module 2 from exceeding a given pressure. Pressure release valve 12 is adapted to be coupled to pressure infuser bag module 2 in each of the user selected configurations. In the illustrated embodiment, pressure release valve 12 is coupled to manual pump module 6. Nevertheless, pressure release valve 12 remains coupled to pressure infuser bag module 2 due to the fact that, in the illustrated embodiment, manual pump module 6 is adapted to be operable in conjunction with pressure infuser bag module 2 in each of the potential configurations.

While pressure infuser apparatus 1 comprises a pressure infuser bag module 2, a motorized pump module 4, and a manual pump module 6 in the illustrated embodiment, pressure infuser apparatus 1 can comprise a variety of modules and elements combined in a variety of configurations within the scope and spirit of the present invention. For example, the types of pumps that can be utilized in the context of the present invention are not limited to motorized pumps and manual pumps; pressurized pumps, chemical pumps, and the like can also be used. Representative embodiments of the present invention will be discussed in greater detail with reference to FIGS. 2–8.

Figure 2:
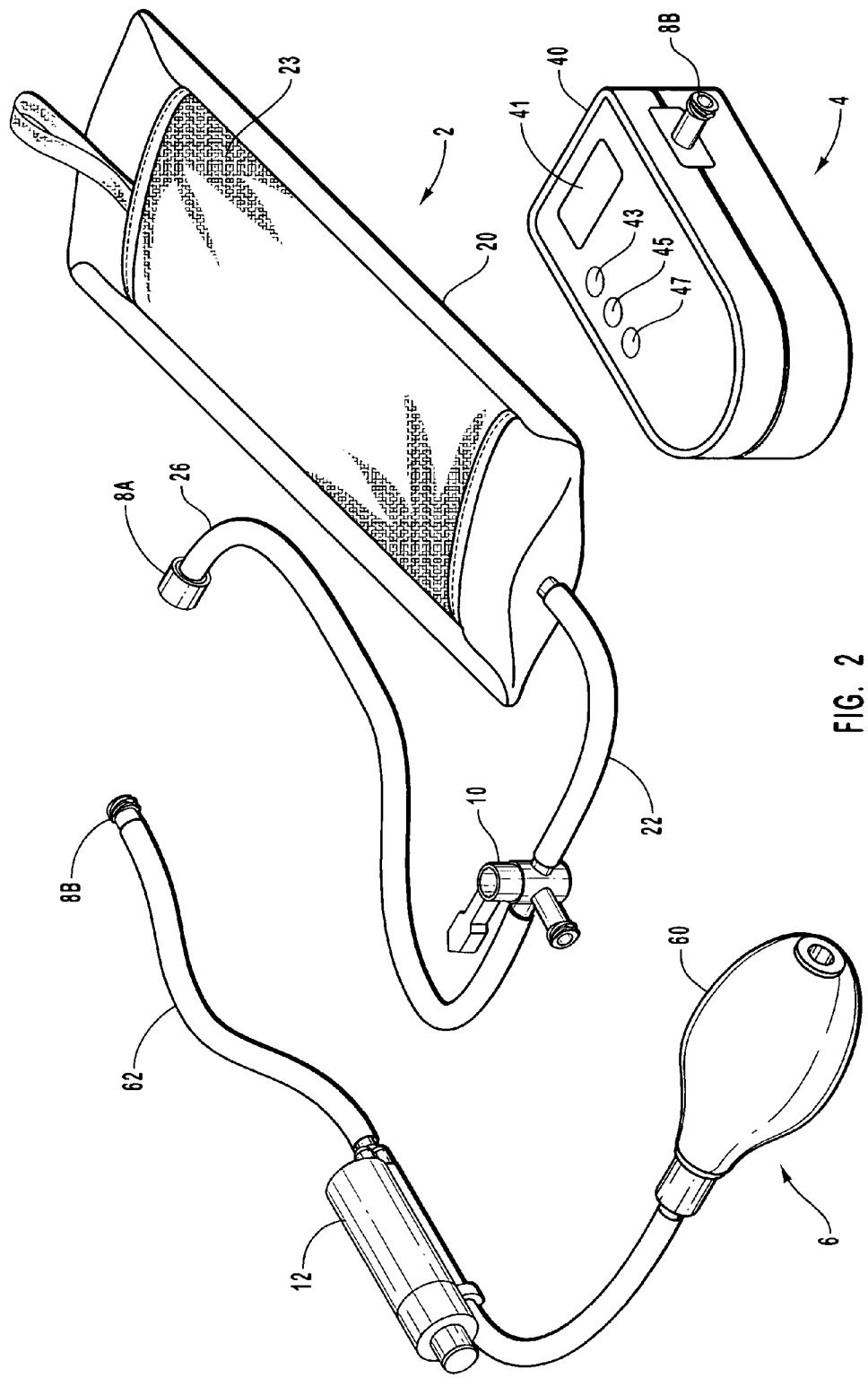
FIG. 2 shows the pressure infuser apparatus of the present invention illustrating the motorized pump module and the manual pump module disconnected from the pressure infuser bag module.

FIG. 2 depicts a configuration pressure infuser apparatus 1 in which motorized pump module 4 and manual pump module 6 are disconnected from pressure infuser bag module 2. There is also shown pressure infuser bag module 2, motorized pump module 4, and manual pump module 6 in greater detail.

Pressure infuser bag module 2 comprises a pressure infuser bag 20, sleeve 23, and tube 22. Sleeve 23 is adapted to hold an infusate bag (not shown). An infusate bag typically comprises a pliant bag filled with infusate fluid to be delivered to a patient. A wide variety of infusate fluids can be utilized including, but not limited to, saline, medicines, blood, plasma, Total Parental Nutrition (TPN), nutritional supplements, vitamins, or the like. The infusate fluids can be delivered to the patient in a variety of manners including, but not limited to, intravenously, gastrointestinally, intramuscularly, or by other methods known in the medical field.

A user inflates pressure infuser bag 20 to increase the pressure on the infusate bag and correspondingly on the infusate fluid. By increasing the pressure on the infusate fluid, the infusate is delivered to the user at a quicker rate than by mere suspension delivery. Additionally, increasing the pressure on the infusate fluid by utilizing a pressure infuser bag 20 allows ambulation of a patient without requiring suspension of infusate bag. This allows the infusate bag and pressure infuser apparatus 1 to be place next to the patient on a hospital bed or on the patient's lap during ambulation.

Tube 22 of pressure infuser bag module 2 allows the user to inflate pressure infuser bag 20. Tube 22 provides a conduit to pump modules 4, 6 allowing inflation of pressure infuser bag 20. Tube 22 can comprise rubber, plastic, or other tubing materials or any other known mechanism for transmitting air pressure to pressure infuser bag 20.

In the illustrated embodiment, stop cock 10 is coupled to tube 22 of pressure infuser bag module 2. Stop cock 10 comprises a three-way stop cock allowing the user to maintain the pressure in pressure infuser bag 20 when pressure infuser bag module 2 is not coupled with either motorized pump module 4 or manual pump module 6 as is shown in FIG. 2. Additionally, stop cock 10 allows the user to release air pressure from the pressure infuser bag 20 when motorized pump module 4 and/or manual pump module 6 is coupled to pressure infuser bag module 2.

Motorized pump module 4 of FIG. 2 comprises motorized pump 40. Motorized pump 40 is adapted to inflate the pressure infuser bag quickly and efficiently with minimum effort by the user. In the illustrated embodiment, motorized pump 40 comprises a display 41, a first actuation button 43, a second actuation button 45, and a third actuation button 47. Display 41 is adapted to indicate the air pressure in pressure infuser bag 20. Display 41 can be adapted to indicate other parameters of pressure infuser apparatus 1 such as lack of change in air pressure, low battery power, user selected settings, or the like. Such parameters can be useful for a variety of reasons. For example, lack of change in air pressure can indicate that the infusate bag is empty or that the delivery line is obstructed. Display 41 can comprise any of a variety of displays that can relate information to a user including, but not limited to, indicator lights, a Liquid Crystal Display (LCD), or a Light-Emitting Diode (LED) display. In alternative embodiments of the present invention, motorized pump 40 does not include a display. Where motorized pump 40 does not include a display, the user can control the air pressure by observing indicia on pressure release valve 12 or by utilizing a motorized pump that automatically controls air pressure.

Actuation buttons 43, 45, and 47 allow a user to inflate the pressure bag by pressing a button. In one embodiment of the present invention, actuation buttons 43, 45, 47 enable a one-touch actuation of motorized pump 40. Upon pressing one of actuation buttons 43, 45, or 47, motorized pump 40 automatically inflates pressure infuser bag 20 to a given pressure. In another embodiment, actuation buttons 43, 45, 47 represent varying air pressures. For example, when a user selects first actuation button 43 motorized pump 40 automatically inflates pressure infuser bag 20 to an air pressure of 100 millimeters mercury. Actuation button 45 and 47 inflate pressure infuser bag 20 to an air pressures of 200 and 300 millimeters mercury. In yet another embodiment, motorized pump 40 can be adapted to automatically maintain the selected air pressure. For example, the motorized pump 40 can be adapted to automatically maintain the air pressure of the pressure infuser bag within a given range to ensure that the air pressure of the pressure infuser bag exceeds the mean arterial pressure and/or maintain the patency of the delivery line to the patient. The method of actuating motorized pump 40 and the manner in which motorized pump 40 inflates pressure infuser bag 10 can vary without departing from the scope or spirit of the present invention. For example, in one embodiment motorized pump 40 includes a single actuation button that must be held down by user until the desired air pressure is attained. Motorized pump 40 will be discussed in greater detail with respect to FIG. 4.

With reference now to manual pump module 6 of FIG. 2. Manual pump module 6 comprises a manual pump 60 and tube 62. Manual pump 60 allows a user to inflate pressure infuser bag 20 without utilizing a motorized pump. Manual pump 60 can be utilized independently from motorized pump 40, or as a supplement to motorized pump 40. In the illustrated embodiment manual pump 60 comprises a compressible bulb. However, a variety of manual pumps can be utilized within the scope and spirit of the present invention. For example, manual pump 60 can comprise a billows pump, foot pump, or other non-motorized pump.

In the illustrated embodiment there are also shown coupler components 8A, B. Coupler first component 8A and coupler second coupler component 8B comprise coupler 8. In one embodiment of the present invention, coupler 8 comprises a luer coupler. Luer couplers are comprised of a male component and a female component. The male and female components are coupled to modules 2, 4, 6 of pressure infuser apparatus 1. By connecting the male and female components a user can connect the modules of pressure infuser apparatus 1. Where the couplers 8 comprise luer couplers, first coupler component 8A comprises a female coupler while second coupler component 8B comprises a male coupler.

In one embodiment of the present invention, pressure infuser bag module 2 is adapted to be coupled to one or more pump modules. For example, in the illustrated embodiment motorized pump module 4 is configured to be coupled to manual pump module 6 when motorized pump module 4 is coupled to stop cock 10. Coupler 8 is adapted to allow a user to modify the configuration of pressure infuser apparatus 1. Coupler first components 8A are coupled to tube 22 and motorized pump module 4. Similarly, coupler second components 8B are coupled to motorized pump module 4 and tube 62. By utilizing this configuration the coupler first component 8A that is coupled to pressure infuser bag module 2 can be coupled to the coupler second component 8B that is coupled to motorized pump module 4. Thus, coupler 8 can be used to couple pressure infuser bag module 2 to motorized pump module 4. Similarly, by utilizing couplers 8, coupler first component 8A that is coupled to motorized pump module 4 can be coupled to coupler second component 8B that is coupled to tube 62. Thus, coupler 8 can be used to couple manual pump module 6 directly to motorized pump module 4 and indirectly to pressure infuser bag module 2 (as is illustrated in FIG. 1).

Figure 3:
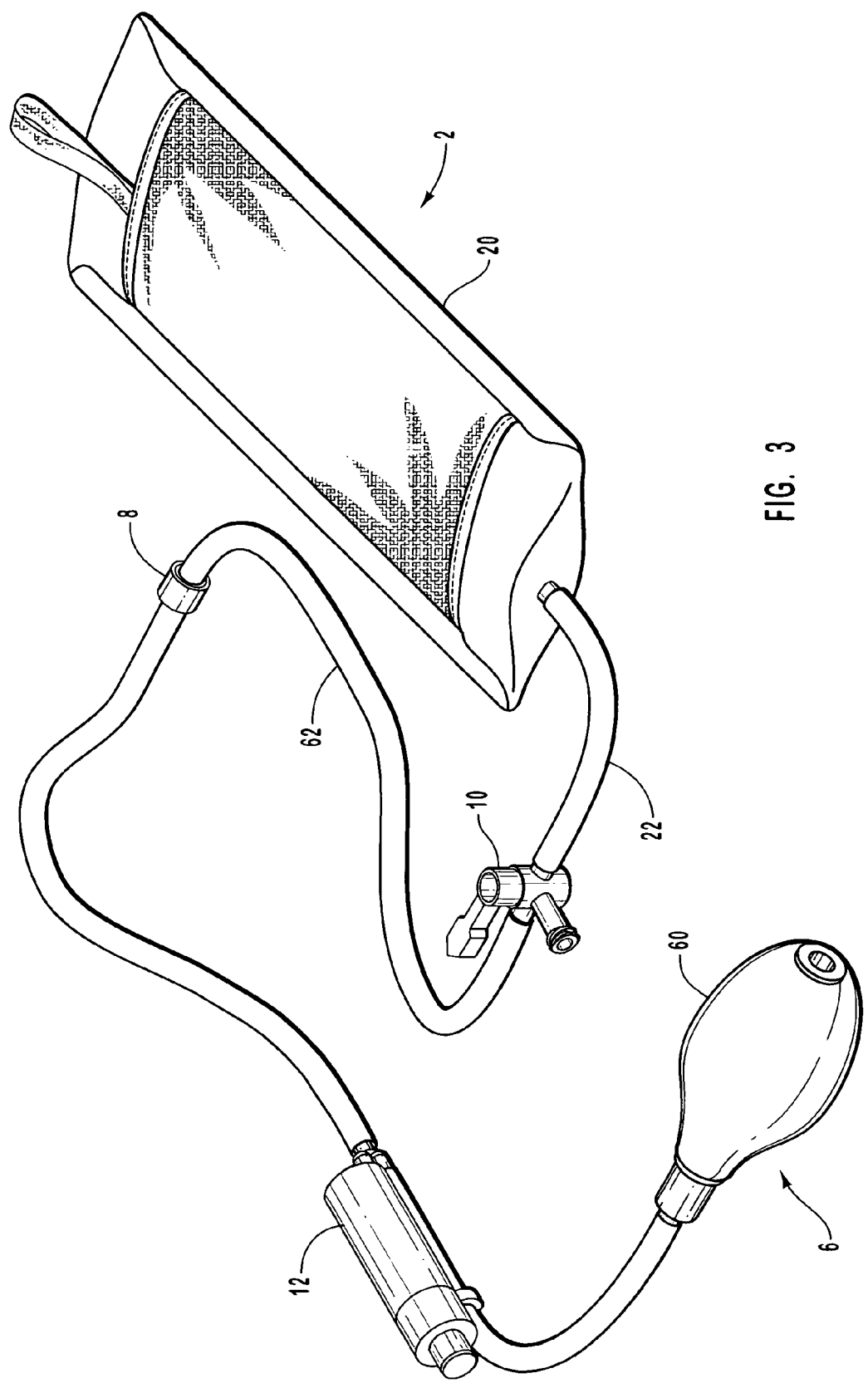
FIG. 3 illustrates a configuration of the pressure infuser apparatus of the present invention in which the motorized pump is disconnected from the pressure infuser bag module and the manual pump module is coupled to pressure infuser bag module.

In the embodiment, couplers 8 not only allow the modules to be coupled together, it also allows them to be disconnected and reconnected in alternative configurations. For example, the configuration of couplers 8 illustrated in FIG. 2 allows first coupler 8A that is connected pressure infuser bag module 2 to be coupled to second coupler 8B that is connected to manual pump module 6 (as illustrated in FIG. 3). This is accomplished by disconnecting first and second coupler components 8A,B connected to tube 22, motorized pump module 4, and tube 62 and recoupling coupler first component 8A connected to tube 22 and coupler second component 8B connected to tube 62.

In an alternative embodiment of the present invention, pressure infuser apparatus 1 is adapted such that pressure infuser bag module 2 can be coupled to a single pump module. Where pressure bag module 2 is adapted to be coupled to a single pump module, first coupler component 8A is coupled to tube 22 of pressure infuser bag module. A second coupler component 8B is coupled to each of the plurality of pump modules. For example, a second coupler component 8B is coupled to motorized pump module 4 and manual pump module 6. By coupling second coupler components 8B to motorized pump module 4 and manual pump module 6, a user is permitted to interchangeably couple motorized pump module 4 and manual pump module 6 to pressure infuser module 2.

One advantage of utilizing a modular pressure infuser apparatus is that the modules can be manufactured separately. Because hospitals often dispose of pressure infuser bags, the hospital only needs to replace the pressure infuser bag module 2 and not the entire pressure infuser apparatus 1. By placing many of the elements of pressure infuser apparatus 1 in reusable modules, pressure infuser bags 20 can be manufactured more inexpensively.

As will be appreciated by those skilled in the art, the configuration of the modular pressure infuser apparatus is not limited to the illustrated embodiment. A variety of types and configurations of modules can comprise motorized pump. For example, the motorized pump can include a signal mechanism such as an alarm. The alarm can be configured to indicate a given state of the pressure infuser bag, such as a pending exhaustion of infusate in the infusate bag or a pending or actual loss of patency of the delivery line. The alarm can provide a visual or audible cue of the state of the pressure infuser bag. The alarm can be coupled to the modular pressure infuser apparatus in a variety of ways, including but not limited to, being coupled to the motorized pump module.

With reference now to FIG. 3 there is shown an alternative configuration of pressure infuser apparatus 1 of the present invention in which motorized pump module 4 is removed from pressure infuser bag module 2 and manual pump module 6 is coupled to pressure infuser bag module 2. FIG. 3 also illustrates how couplers 8 not only allow the modules to be coupled together, but also allows them to be disconnected and reconnected in alternative configurations. For example, the configuration of couplers 8 illustrated in FIG. 2 allows first coupler 8A, which is connected pressure infuser bag module 2, to be coupled to second coupler 8B, which is connected to manual pump module 6. This is accomplished by disconnecting first and second coupler components 8A,B connected to tube 22, motorized pump module 4, and tube 62 and recoupling coupler first component 8A connected to tube 22 and coupler second component 8B connected to tube 62.

The illustrated configuration in which motorized pump module 4 is removed from pressure infuser apparatus 1 can be utilized where a patients' condition does not require the ability to rapidly inflate pressure infuser bag 20. Thus, where the patient's condition stabilizes after surgery, trauma, or critical care, motorized pump module 4 can quickly be removed from pressure infuser apparatus 1. This allows the number of motorized pump units that must be utilized by the hospital to be limited without requiring the medical staff to continually and inconveniently change pressure infuser apparatuses.

Another advantage of utilizing a modular pressure infuser apparatus is that the modules can be separately manufactured. Because hospitals often dispose of pressure infuser bag 20, the hospital only needs to replace pressure infuser bag module 2 rather than the entire pressure infuser apparatus 1. By placing many of the elements of pressure infuser apparatus 1 in reusable modules, pressure infuser bags 20 can be manufactured more inexpensively.

Figure 4:
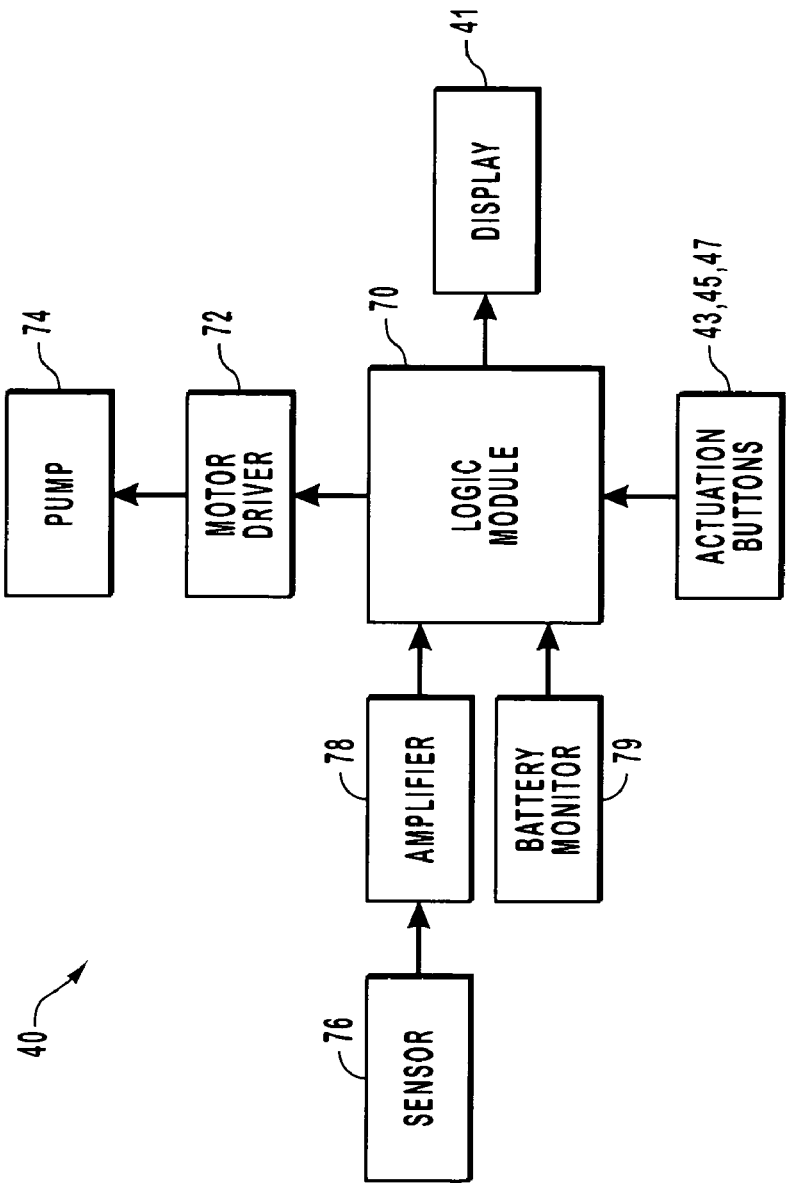
FIG. 4 is a block diagram illustrating various components of the motorized pump.

With reference now to FIG. 4, there is shown a block diagram illustrating various components of motorized pump 40. In the illustrated embodiment, motorized pump 40 comprises a display 41, actuation buttons 43, 45, 47, a logic module 70, a motor driver 72, a pump 74, a sensor 76, an amplifier 78, and a battery monitor 79. Display 41 provides a mechanism for indicating the air pressure in the air pressure bag 20. Actuation buttons 43, 45, 47 provide a mechanism for allowing a user to control the inflation of the air pressure bag 20. A more detailed discussion of display 41 and actuation buttons 43, 45, 47 is included with reference to FIG. 2.

Logic module 70 comprises a mechanism for controlling the operation of motorized pump 40. Logic module 70 can comprise a microprocessor, logic circuitry or similar mechanism capable of providing control functionality to the motorized pump 40. Logic module 70 can be configured to utilize software enabling a variety of functionality and/or control functions. For example, the software can be configured to actuate an alarm after a selected number of inflation intervals, to indicate a loss of patency in the delivery line, and/or maintain the pressure in the pressure infuser bag. Motor driver 72 provides the motorized force required to pump air into the pressure infuser bag 20. Motor driver 72 can comprise any of a variety of mechanical, electromechanical, electrical, chemical or other drivers known in the art.

Pump 74 utilizes the energy provided by motor driver 72 to pump the air into pressure infuser bag 20. A variety of known pumps mechanisms can be utilized for pump 74. Sensor 76 allows motorized pump 40 to detect the air pressure in pressure infuser bag 20. Amplifier 78 amplifies the sensor signal to allow logic module 70 to read and analyze the sensor signal. Finally, a battery monitor 79 permits the system to detect the power level of the battery to prevent unanticipated failure of motorized pump 40. FIGS. 5A-C provide a perspective view of pressure release valve 12. Pressure release valve 12 is configured to prevent the pressure of pressure infuser bag module 2 from exceeding a given pressure. Pressure release valve 12 is adapted to be coupled to pressure infuser bag module 2 in each of the user selected configurations of pressure infuser apparatus 1. In the illustrated embodiment, pressure release valve 12 comprises a known pressure release valve. However, as will be appreciated by those skilled in the art, the exact type and configuration of pressure release valve can vary without departing from the scope and spirit of the present invention. Returning to a discussion of the illustrated embodiment, pressure release valve 12 comprises a valve housing 120 and a pressure indicator 122. In the illustrated embodiment, pressure indicator 122 extends from valve housing 120 as the air pressure in pressure infuser bag 20 increases.

Pressure indicator 122 includes a plurality of indicia 124, 126, 128, 130 for indicating the air pressure in pressure infuser bag 20. Indicia 124, 126, 128, 130 are intended to be illustrative of indicia that can be utilized to indicate the air pressure of pressure infuser bag 20 and in no way should be considered to limit the type or configuration of indicia that can be utilized. For example, the indicia can include one or more lines, regions, lights, and/or displays positioned in a variety of locations on any of a variety of pressure release valves.

In the illustrated embodiment, indicia 124 denotes a first amount of air pressure. Indicia 126, shown in FIG. 5A, denotes a second amount of air pressure. Indicia 128, shown in FIG. 5B, denotes a third amount of air pressure. Indicia 130, shown in FIG. 5C, denotes a fourth amount of air pressure. For example, first indicia 124 indicates that the pressure in pressure infuser bag 20 is greater than 100 millimeters mercury. Second indicia 126 indicates that the pressure in the pressure infuser bag 20 is greater than 200 millimeters mercury. Third indicia 128 indicates that the pressure in pressure infuser bag 20 is greater than 300 millimeters mercury. The fourth indicia 130 indicates that the pressure in pressure infuser bag 20 is close to exceeding a given safe parameter. In the illustrated embodiment, once the air pressure exceeds 300 millimeters mercury, as shown in FIG. 5C, pressure relief valve 12 is adapted to release air pressure until the air pressure in pressure infuser bag 20 approximates 300 millimeters mercury.

Figure 6:
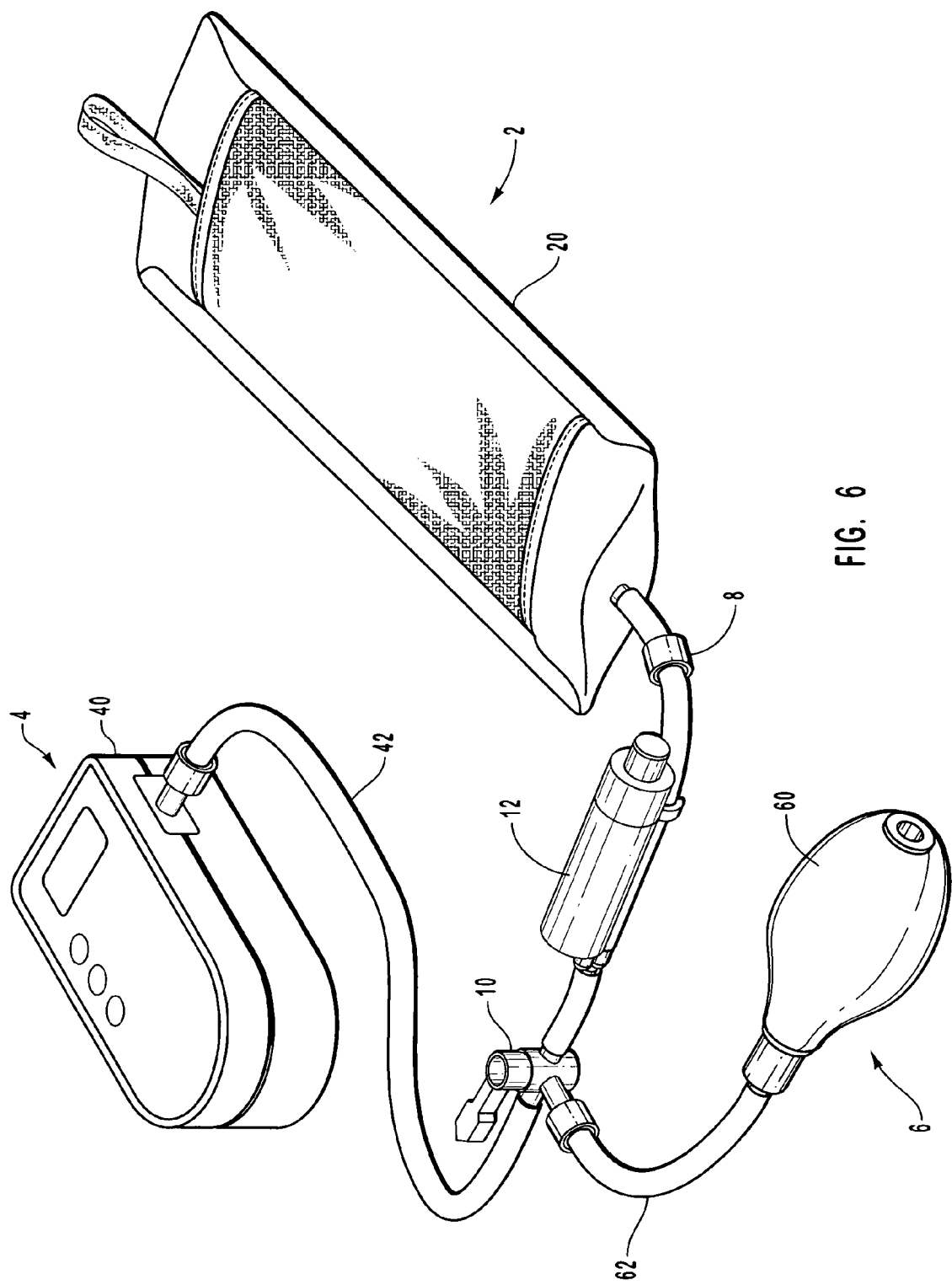
FIG. 6 is a perspective view of one configuration of the pressure infuser apparatus of the present invention.

With reference now to FIG. 6, there is shown a perspective view of one configuration of pressure infuser apparatus 1 of the present invention. In the embodiment, a single tube 22 is coupled to pressure infuser bag 20. Tube 22 provides a conduit through which motorized pump module 40 and/or manual pump module 6 are able to provide air pressure to inflate pressure infuser bag 20. Tube 22 includes a coupler 8. In embodiments in which the pressure infuser bag 20 is disposable, coupler 8 allows the bag and a portion of tube 22 to be disconnected and thrown away. Several of the more expensive components of pressure infuser apparatus 1, such as motorized pump 40, manual pump 6, pressure release valve 12, and stop cock 10 are reusable, thus reducing the cost of manufacturing the disposable components of pressure infuser apparatus 1.

In the illustrated embodiment, stop cock 10 comprises a four-way stop cock to which pressure infuser bag module 2, motorized pump module 4, and manual pump module 6 are coupled. By utilizing a four-way stop cock, stop cock 10 can be coupled to tube 42 and tube 62. In this embodiment, manual pump module 6 does not have to be recoupled to pressure infuser bag 20 when motorized pump module 4 is removed. Stop cock 10 allows the air pressure in pressure infuser bag 20 to be maintained when motorized pump module 4 is removed. In the illustrated embodiment pressure release valve 12 is coupled to the tube that lies between stop cock 10 and coupler 8. This allows pressure release valve 12 to regulate the air pressure in pressure infuser bag 20 notwithstanding the position of stop cock 10.

In the illustrated embodiment motorized pump module 4 comprises both a motorized pump 40 and tube 42. To remove motorized pump module 4 a user uncouples tube 42 from stop cock 10. In one embodiment of the present invention a coupler allows the user to couple and uncouple tube 42 and stop cock 10. In an alternative embodiment, stop cock 10 is configured such that tube 42 can be directly and removeably coupled to stop cock 10.

Manual pump module 6 is configured to be coupled to stop cock 10. In one embodiment manual pump module 6 is permanently coupled to stop cock 10. In an alternative embodiment manual pump module 6 is releasably coupled to stop cock 10 allowing the user to connect and disconnect manual pump module 6. As with motorized pump module 4, a coupler provides the connection to stop cock 10.

Figure 7:
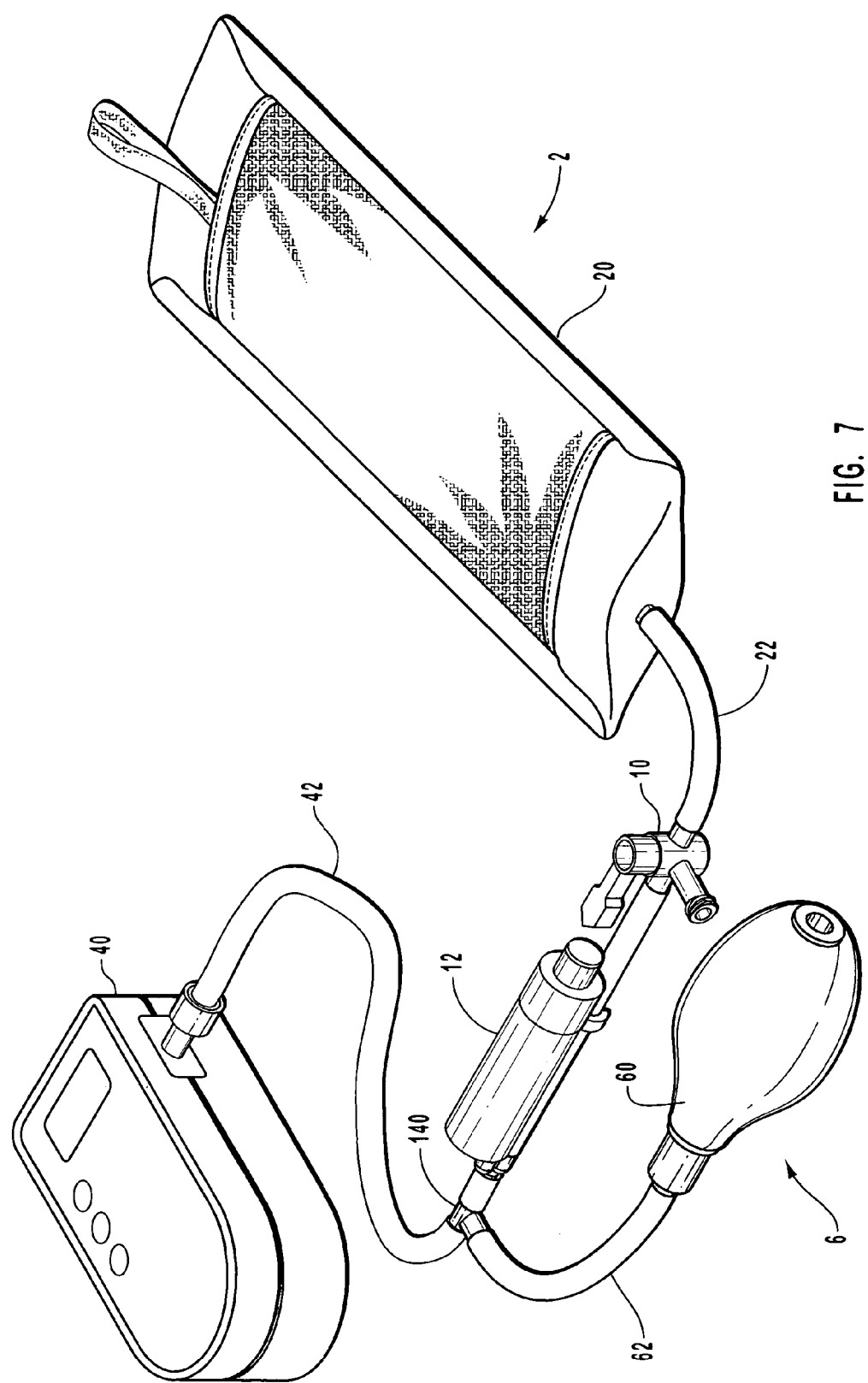
FIG. 7 is a perspective view of yet another configuration of the pressure infuser apparatus of the present invention.

FIG. 7 is a perspective view of yet another configuration of pressure infuser apparatus 1 of the present invention. In the illustrated embodiment stop cock 10 comprises a three-way stop cock. A Y joint coupler 140 is included for coupling both manual pump module 6 and motorized pump module 2 to stop cock 10. The branches of the Y joint coupler 140 permits tubing from two pump modules to be coupled to the pressure infusion bag 20. In one embodiment, each branch of Y joint coupler 140 is adapted to automatically seal when either motorized pump module 40 or manual pump module 60 is removed from the branch. In an alternative embodiment, sealing mechanisms such as valves or stop cocks are provided between Y joint coupler 140 and motorized pump 40 and/or manual pump 60. The sealing mechanisms allow the user to maintain the air pressure in pressure infuser bag 20 when motorized pump 40 and/or manual pump 60 are removed from pressure infuser apparatus 1. For example, in one embodiment, a stop cock is coupled between Y joint coupler 140 and motorized pump 40. The user can utilize the stop cock to maintain the pressure in pressure infuser bag 20 when motorized pump module is detached from pressure infuser bag module 1.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A kit containing a plurality of modularized components for assembling a modularized pressure infuser apparatus for applying pressure to an infusate bag to facilitate the delivery of an infusate fluid to a patient, the modularized components of the pressure infuser apparatus allowing a user to modify the configuration of the pressure infuser apparatus to correspond to the infusion needs of the patient, the pressure infuser apparatus kit comprising the following components:

(a) a pressure infuser bag module comprising,
  a pressure infuser bag for applying pressure to the infusate bag,
  a first length of tubing connected at one end to the pressure infuser bag;
(b) a motorized pump for applying pressure to inflate the pressure infuser bag, the motorized pump comprising a coupler for connecting the motorized pump to a length of tubing;
(c) a manual pump module comprising,
  a manual pump for inflating the pressure infuser bag, and
  a second length of tubing connected at one end to the manual pump;
(d) a pressure relief valve for preventing the pressure of the pressure infuser bag from exceeding a given pressure, the pressure relief valve, the pressure relief valve comprising inlet and outlet connectors for permitting connection to tubing at inlet and outlet ends of the valve; and
(e) second and third lengths of tubing, each having a connector at at least one end thereof; and
the kit components (a)–(e) being adapted for connection of a pressure infusion apparatus having at least any one of the following configurations:
  (1) the pressure infuser bag module being connected to the pressure relief valve, which in turn is connected through a length of tubing to the manual pump;
  (2) the pressure infuser bag module being connected to the pressure relief valve, which in turn is connected through a length of tubing to the motorized pump;
  (3) the pressure infuser bag module being connected to the motorized pump, which is then connected through another length of tubing to the pressure relief valve, which is then connected to the manual pump; or
  (4) the pressure infuser bag module being connected to the pressure relief valve, which is then connected through a length of tubing to the motorized pump, and also being connected to the manual pump module.

2. A kit containing a plurality of modularized components for assembling a modularized pressure infuser apparatus for applying pressure to an infusate bag to facilitate the delivery of an infusate fluid to a patient, the modularized components of the pressure infuser apparatus allowing a user to modify the configuration of the pressure infuser apparatus to correspond to the infusion needs of the patient, the pressure infuser apparatus kit comprising the following components:

(a) a pressure infuser bag module comprising,
  a pressure infuser bag for applying pressure to the infusate bag,
  a first length of tubing connected at one end to the pressure infuser bag;
(b) a motorized pump for applying pressure to inflate the pressure infuser bag, the motorized pump comprising a coupler for connecting the motorized pump to a length of tubing;
(c) a manual pump module comprising,
  a manual pump for inflating the pressure infuser bag, and
  a second length of tubing connected at one end to the manual pump;
(d) a pressure relief valve for preventing the pressure of the pressure infuser bag from exceeding a given pressure, the pressure relief valve, the pressure relief valve comprising inlet and outlet connectors for permitting connection to tubing at inlet and outlet ends of the valve;
(e) second and third lengths of tubing, each having a connector at at least one end thereof; and
(f) a two-way stopcock; and
the kit components (a)–(f) being adapted for connection of a pressure infusion apparatus having at least any one of the following configurations:
  (1) the pressure infuser bag module being connected to the pressure relief valve, which in turn is connected through a length of tubing to the manual pump;
  (2) the pressure infuser bag module being connected to the pressure relief valve, which in turn is connected though a length of tubing to the motorized pump;
  (3) the pressure infuser bag module being connected to the two-way stopcock, which in turn is connected to the motorized pump, which is then though another length of tubing to the pressure relief valve, which is then connected to the manual pump;
  (4) the pressure infuser bag module being connected to the pressure relief valve, which connected though a length of tubing to the two-way stopcock, which in turn is connected though a length of tubing to the motorized pump, and the two-way stopcock also being connected to the manual pump module; or
  (5) the pressure infuser bag module being connected to the two-way stopcock, which is connected though a length of tubing to the pressure relief valve, which in turn is connected though a length of tubing to the motorized pump, and the pressure relief valve also being connected to the manual pump module.

* * * * *